United States Patent
Yoshimura et al.

[11] Patent Number: 5,946,029
[45] Date of Patent: Aug. 31, 1999

[54] IMAGE PROCESSING PROCESS

[75] Inventors: Kazunari Yoshimura; Ryosuke Mitaka; Kuninori Nakamura; Yasuyuki Yuki, all of Kadoma, Japan

[73] Assignee: Matsushita Electric Works, Ltd, Osaka, Japan

[21] Appl. No.: 08/867,101

[22] Filed: Jun. 2, 1997

[30] Foreign Application Priority Data

Jun. 25, 1996 [JP] Japan ..................................... 8-185486

[51] Int. Cl.$^6$ ....................................................... H04N 7/18
[52] U.S. Cl. ........................................... 348/131; 382/141
[58] Field of Search .................................. 348/86, 87, 88, 348/92, 125, 126, 128, 131; 382/141, 145, 147; H04N 7/18

[56] References Cited

U.S. PATENT DOCUMENTS

| | | | |
|---|---|---|---|
| 5,515,452 | 5/1996 | Penkethman | 382/141 |
| 5,631,733 | 5/1997 | Henley | 348/126 |
| 5,652,805 | 7/1997 | Ooenoki | 382/141 |
| 5,781,649 | 7/1998 | Brezoczky | 382/141 |

*Primary Examiner*—Howard Britton

[57] ABSTRACT

An image processing process disposes a television (TV) camera for observing a direct reflection of an incident light in a direction substantially coinciding with rolling direction of such detection object as a laminating substrate or the like, and observes a direct reflection component of the light with mutual positional relationship between the TV camera, object and a light source varied. Measuring thus sequentially the brightness with the angle of incident light varied, a lighting angle at which the brightness of reflection is the largest, that is, an incident angle of direct reflection light is obtained with respect to respective measuring points on the object, and an image representing a distribution of incident angles of the direction reflection light can be obtained by obtaining the incident angles of the direct reflection light with respect to the whole points on the detection object.

20 Claims, 13 Drawing Sheets

$I_0(x,y)$ $I_1(x,y)$ $I_n(x,y)$

RP

RI

FIG. 15
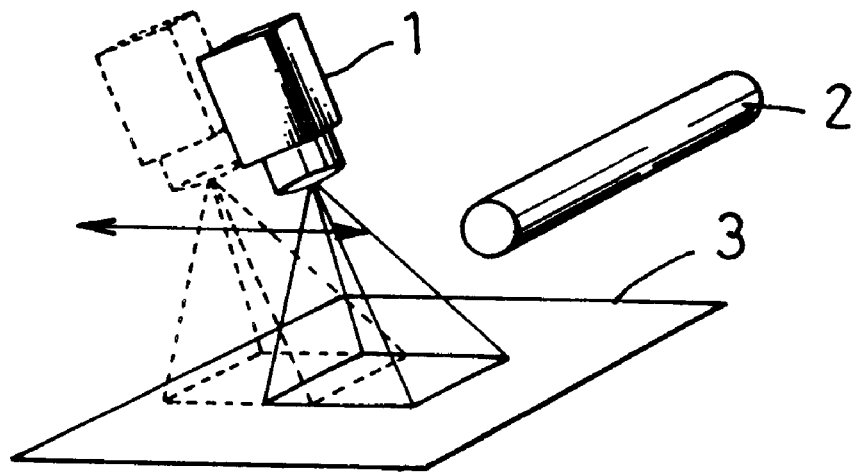
FIG. 16(a)    FIG. 16(b)
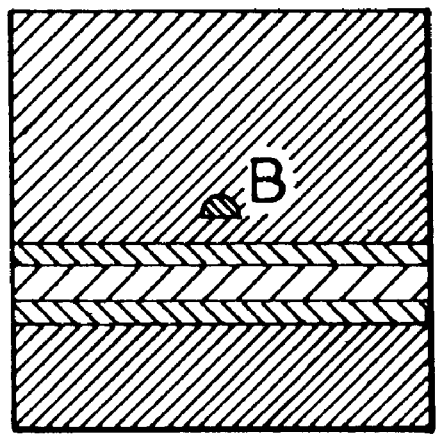 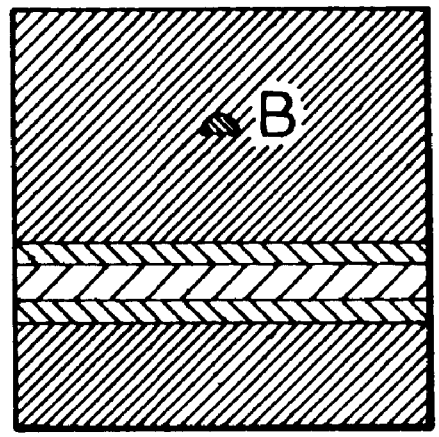

IMAGE PROCESSING PROCESS

BACKGROUND OF THE INVENTION

This invention relates to an image processing process which can realize a measurement of three dimensional configuration of an object, as well as an image processing process including an object's surface-defect detecting arrangement for highly precisely detecting at a high speed a microfine undulatory defect and any defect appearing as a varying density information on laminating substrate and the like.

DESCRIPTION OF RELATED ART

As one of measures for determining or measuring three dimensional configuration of an object through a processing of images obtained with a television (TV) camera, there has been suggested in Japanese Patent Laid-Open Publication No. 63-83873 by Ogata et al. a process for measuring the three dimensional configuration of an object on the basis of reflectance with a plurality of images obtained by sequentially lighting a plurality of light sources (an illuminance difference stereograph). In this process, a reflected light intensity information (reflectance map) representing a relation between planar direction of the surface of object based on the images upon illumination of a reference object with respective luminaires and the lightness or brightness measured by the TV camera is obtained, gradients of surface elements of an actual object of the measurement are obtained by collating a brightness measured by the TV camera through similar illumination of the actual object of the respective luminaires with the above reflectance map, and the three dimensional configuration of the actual object is constituted again with the gradients employed.

As a process for detecting the defect present on a lustered object, there has been suggested in Japanese Patent Laid-Open Publication No 3-296408 by Yamatake et al. a process utilizing an interference of laser beam, in which a copper clad laminate manufacturing method performs an etching work with respect to copper layers formed to be several ten microns on both surfaces of respective insulating substrates, and a plurality of such copper clad substrates are laminated to be formed into final products, whereupon flaws, dents, rust, stains or the like defect happens to occur on the surfaces of the substrates before being laminated and requires to be preliminarily detected. The surfaces of the substrates are further caused to be dull in the metallic luster due to very fine unevenness of about several $\mu$m occurring upon being rolled, and general formation of the insulating substrate with fabric member impregnated with a resin should result in an appearance of mesh of the fabric member. In the known defect detecting process, the detection of the unevenness present regularly on all surfaces and of very fine defects on the plane having the semi-lustered planes is executed by irradiating a laser beam at a very shallow angle with respect to the planes, and the defect is detected by observing an interference band occurring due to microfine structure at the surface upon reflection of the beam thereupon. To be more concrete, the beam projected from a laser source is expanded into a slit shape by a lens, and the slit-shape beam is made incident through a projecting lens on a zone in a predetermined width of the substrate to be reflected thereon at a shallow angle. Thus reflected light is projected as an interference pattern on the screen disposed in opposition to the laser beam source. In an event where the substrate surface has any flaws, the interference band is to be obserbed, such band is photographed by the TV camera, and the defect can be discriminated through an image processing device.

In the former described process for detecting the three dimensional configuration, however, there has been such problem that, since the reflectance map is constructed as based on an assumption that the surface shape of the object is identical all over the surfaces of the object, this process cannot be applied to an object which involves a fluctuation in the surface reflectance. Further, since an irregular reflection component is employed, the process also is not applicable to a lustered object from which the irregular reflection component cannot be obtained. Further, as the three dimensional configuration is to be obtained with the brightness upon illumination by means of the luminaire made as the reference, the detection is remarkably influenced by a secondary reflect of the illumination.

Further, in the latter described defect detecting process, there are such problems that any foreign matter on the substrate causes the interference band to be remarkably varied to be erroneously detected as being no good. Further, if the substrate involves any warping, the interference band is caused to be out of measuring sight so as not to be normally measured.

So long as the three dimensional configuration cannot be obatined, the defect involving some dents and the defect which does not involve any dent cannot be discriminated from each other. Further, since the interference phenomenon of laser beam is to be utilized, the detection of very fine structure on the substrate surface is remarkably influenced thereby.

SUMMARY OF THE INVENTION

The present invention has been suggested to overcome the foregoing problems, and it is an object of the present invention to provide an image processing process which allows an accurate three dimensional configuration of in particular an object having a color shading or a luster.

It is another object of the present invention to provide an image processing process which includes a defect detecting process capable of stably detecting surface defect of the object with less affection of surface characteristic and foreign matter.

According to the present invention, the above objects can be established by means of an image processing process comprising the steps of the disposing a TV camera for photographing an object and a light source for illuminating the object, obtaining sequentially a plurality of images of the object with the TV camera while relatively varying positional relationship of the light source, object and TV camera so as to sequentially vary the angle of incident illumination light at a plurality of positions on the surface of the object, obtaining a distribution of the angle of incident direct-reflection light at the time when the brightness is the largest at points identical to the plurality of images of different angles of incident illumination light, and obtaining images showing the distribution of the angle of direct-reflection light at a plurality of predetermined points on the surface of the object of detection.

With the above process, it is enabled to measure the surface gradient at all points on the surface of the object of detection, with a simple arrangement.

All other objects and advantages of the present invention shall be made clear in the following description of the invention detailed with reference to preferred embodiments shown in accompanying drawings.

BRIEF DESCRIPTION OF THE DRAWINGS

FIG. 15 is a schematic explanatory view for a device employed in performing another embodiment of the image processing process according to the present invention;

FIGS. 16(a) and 16(b) are explanatory views for an appearance of variation in the positional relationship between the TV camera and the object of detection in the embodiment shown in FIG. 15;

Figure 1:
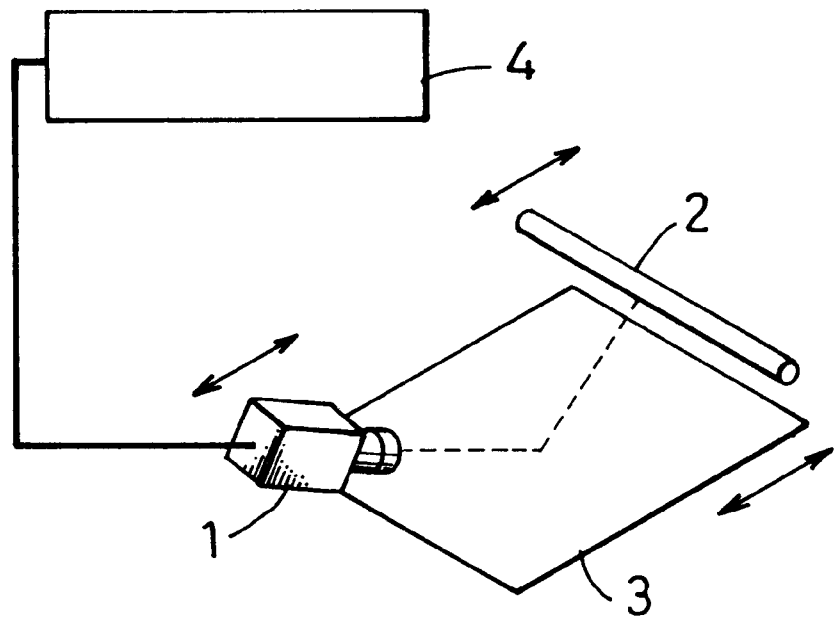
FIG. 1 is an explanatory view for a conceptual arrangement of a device performing an embodiment of the image processing process according to the present invention.

While the present invention shall now be described with reference to the particular embodiments shown in the drawings, it should be appreciated that the intention is not to limit the invention only to these particular embodiments shown but rather to include all alterations, modifications and equivalent arrangements possible within the scope of appended claims.

DETAILED DESCRIPTION OF THE PREFERRED EMBODIMENTS

Referring to an embodiment of the present invention, FIG. 1 shows schematically an image processing device employed in performing the embodiment of the image processing process of the present invention, which device comprises a TV camera 1, a light source 2 and an image processing section 4, so that a surface of such object 3 of detection as a substrate of copper clad laminate, the illuminated surface is photographed by the TV camera 1, and the image photographed by the TV camera is processed at the image processing section 4.

Figure 2:
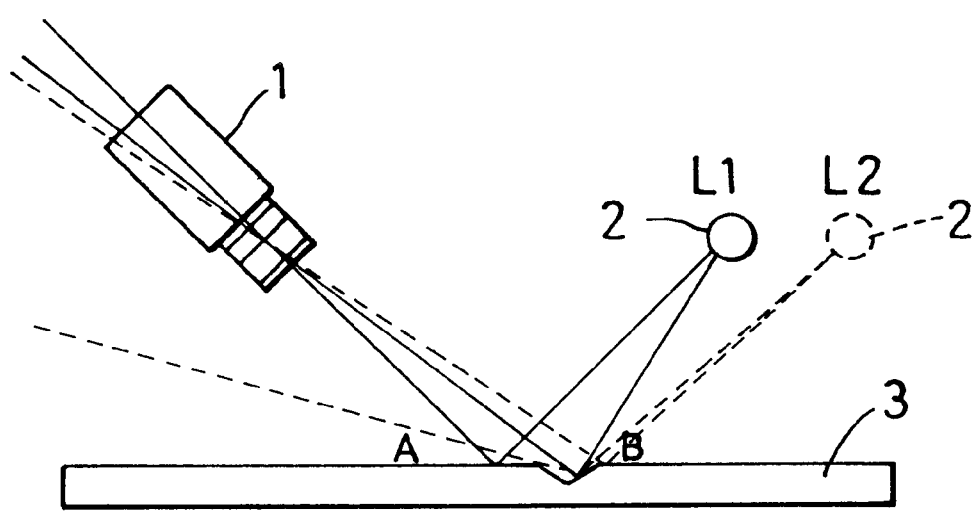
FIG. 2 is a theoretical explanatory view for the arrangement of the embodiment in FIG. 1.
Figure 3:
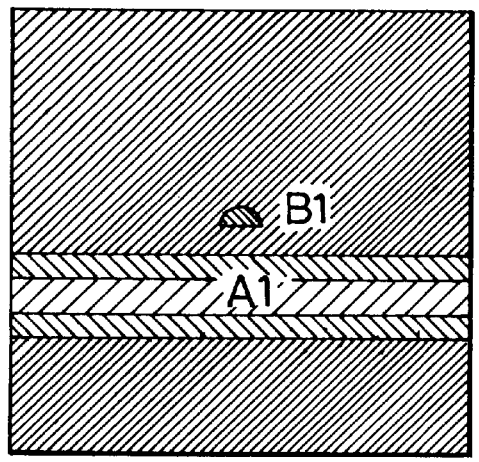
FIG. 3 is a schematic explanatory view of the object as photographed by the TV camera in the arrangement of FIG. 2.
Figure 4:
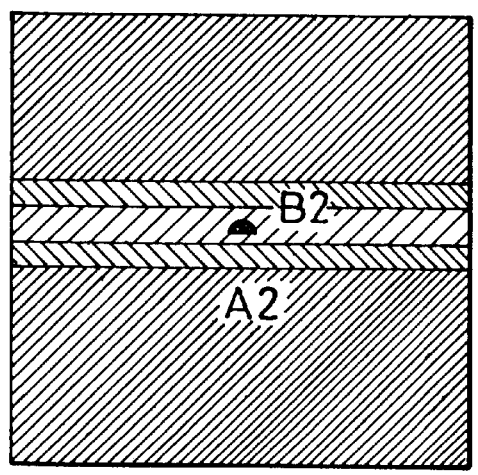
FIG. 4 is another schematic explanatory view of the object as photographed by the TV camera in FIG. 2.
Figure 5:
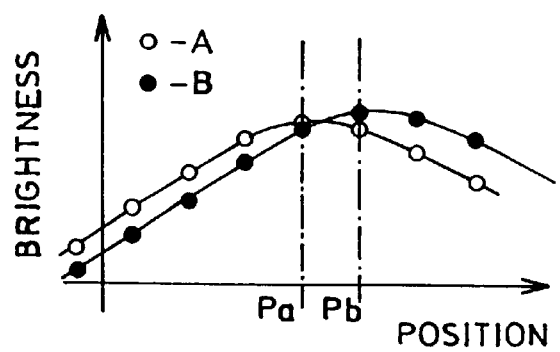
FIG. 5 is an explanatory diagram for variation in the brightness on surfaces of different gradients.

More specifically, unevenness of several $\mu$m is present on the surface of copper layer on the substrate, as caused to occur upon rolling work of the layer in the form of streaks lying in the rolling direction and all over the surface, so that light emitted from the light source 2 will be caused to irregularly reflect by such fine unevenness on the surface, but a strong direct reflection component is caused to be present in a direction of reflection angle along the rolling direction. In the device shown here, therefore, the TV camera 1 is disposed in a direction substantially coinciding with the rolling direction, for observing the direct reflection component, while varying mutual positional relationship of the light source 2, TV camera 1 and detecting object 3 as shown by respective arrows. Images obtained upon this observation with respect to different angles of incident illumination light are as shown, for example, in FIGS. 3 and 4. Now, when the light source 2 is at a position of L1 in FIG. 2, an illuminated part at a position A on the surface of the object 3 is almost flat, and the direct reflection component of the incident light from the source 2 appears in the form of band A extending in lateral directions in FIG. 3. On the other hand, at a defective part in the form of dent B as shown in FIG. 2, there appears such local direct reflection component B1 as shown in FIG. 3. When the light source 2 is at another position B of FIG. 2, the direct reflection component is not observed at part A2 in FIG. 4 corresponding to the position A in FIG. 2 and, instead, a band form direct-reflection component is observed at part B2 in FIG. 4 corresponding to adjacent part to the part B in FIG. 2. In the case of the defective part locally different in surface direction (B in FIG. 2), however, the direct reflection component cannot be obtained. Variation in the brightness at the positions A and B of FIG. 4 when the angle of incident illumination light is varied is as shown in FIG. 5, in which it has been found that the angle of incident illumination light representing the largest brightness (corresponding to positions Pa and Pb of curves) is different between the flat part A shown by a curve of black dots and the defective part B shown by a curve of white dots different in the gradient from the part A. Therefore, by sequentially measuring the brightness while varying the angle of incident illumination light, an angle of illumination at which the brightness becomes the largest, that is, the angle of incident direct-reflection light at the respective measuring points on the object can be obtained and, by obtaining such angle of incident direct-reflection light at many predetermined points on the object, an image representing a distribution of the angles of incident direct-reflection light (angle distribution image) can be obtained.

Figure 6:
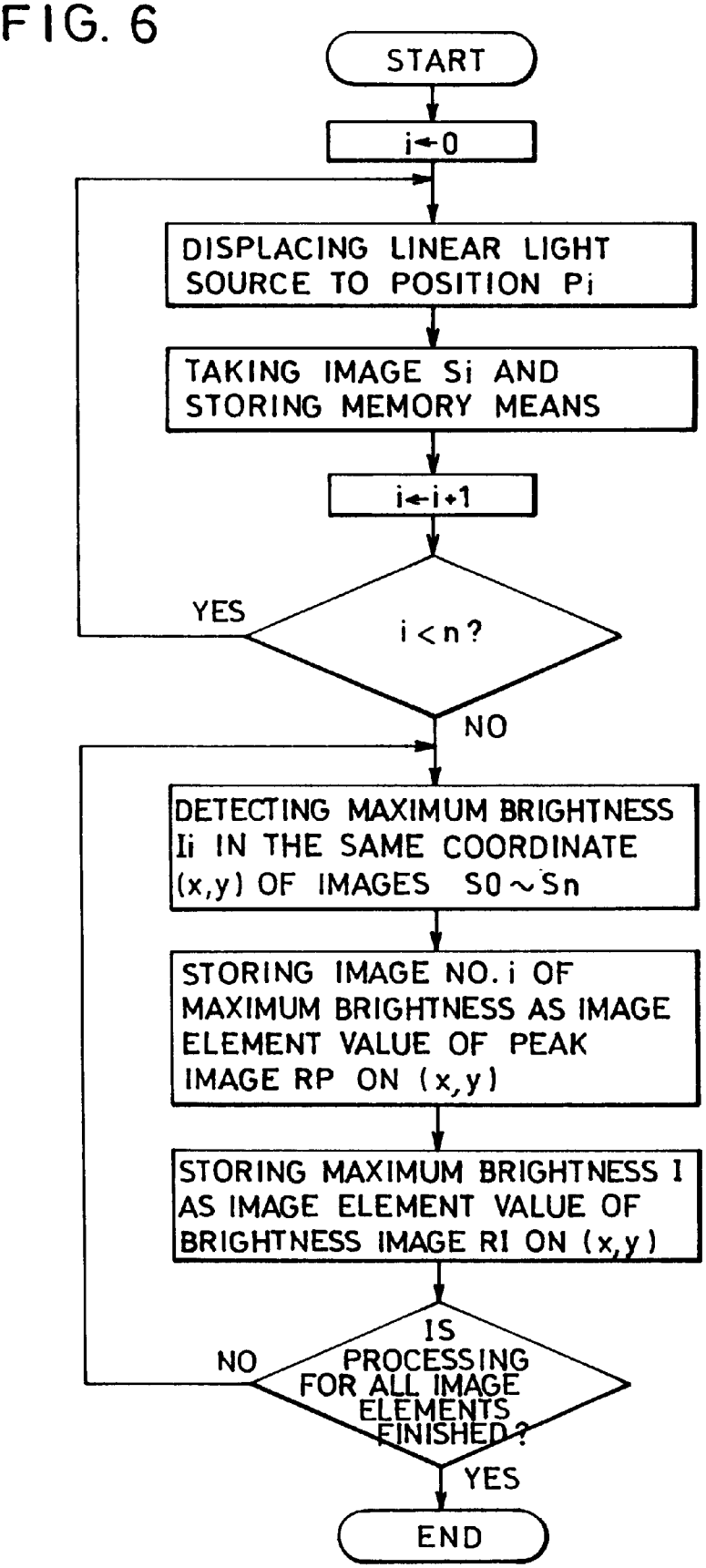
FIG. 6 is a flow chart of the embodiment of FIG. 1.
Figure 7:
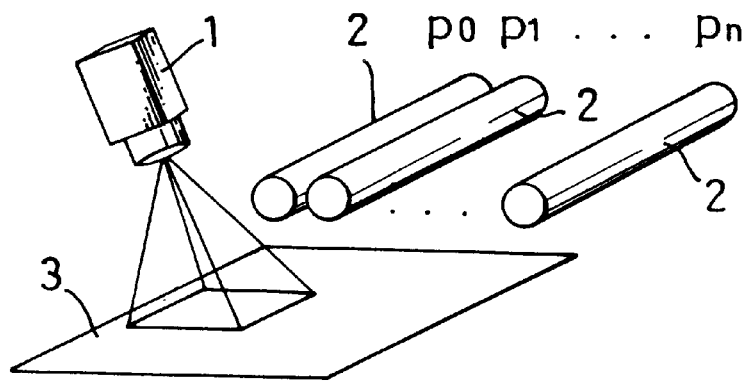
FIG. 7 is an explanatory view for the device in the embodiment of FIG. 1.
Figure 8:
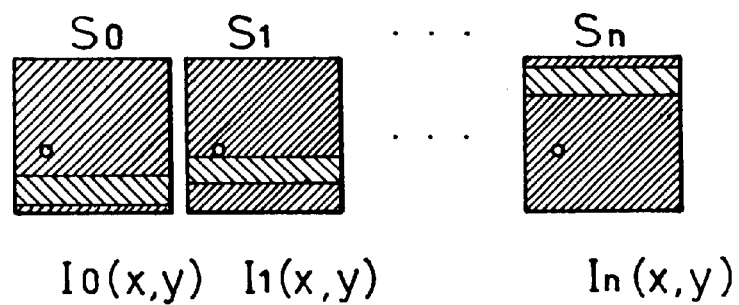
FIG. 8 is an explanatory view for the images obtained with the device of FIG. 7.

Next, the processing operation at the image processing section 4 in the process of the present embodiment shall be described with reference to the flow chart of FIG. 6. First, an instance in which the light source 2 is moved shall be described as an example forming the simplest arrangement. In FIG. 7, the operation of the device performing the present embodiment is shown, and the images obtainable with the TV camera 1 in this operation are shown in FIG. 8.

First, the positions of the TV camera 1, light source 2 and detection object 3 are subjected to an initial setting (i←0) so that the direct reflection component in the event when the detection object 3 is illuminated by the light source 2 will be incident at an end edge portion of the sight of the TV camera 1. Then, the light source 2 is moved and, after every movement of the source 2 by a fixed amount (i←i+1), signals of images in varying density of 256 gradations are input from the TV camera 1 to the image processing section 4. Until the light from the source 2 and directly reflected on the object 3 appears at the opposite end edge portion of the sight, the light source 2 is kept moved from the position p0 to pn, and the images S0 to Sn as in FIG. 8 are taken up.

Next, the brightness I0 to In at the same coordinates (x,y) as the images S0 to Sn is compared in respect of respective picture elements of the images taken up, and an image number "i" showing the largest value and the brightness Ii at the time of the largest value of "i" are obtained. Further, the image number "i" is regarded as a numerical value denoting the angle of illumination, and is recorded as a picture element value at the coordinates (x,y) of the angle distribution image RP. Further, the largest brightness Ii is recorded as a picture element value at the coordinates (x,y) of the brightness distribution image RI.

Figure 9:
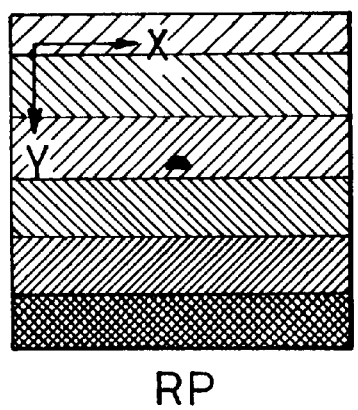
FIG. 9 is an explanatory view for an image of angle distribution obtained in the embodiment of FIG. 1.
Figure 10:
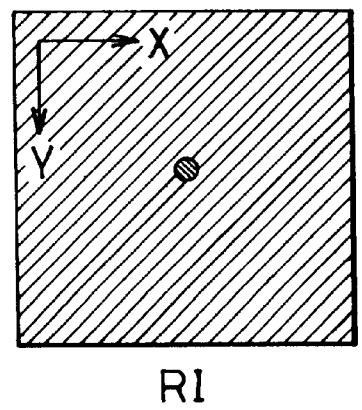
FIG. 10 is an explanatory view for an image of brightness distribution obtained in the embodiment of FIG.
Figure 11:
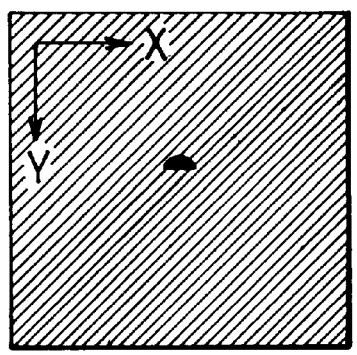
FIG. 11 is an explanatory view for an image of gradient distribution of the surface obtained by converting the image of angle distribution shown in FIG. 9.
Figure 12:
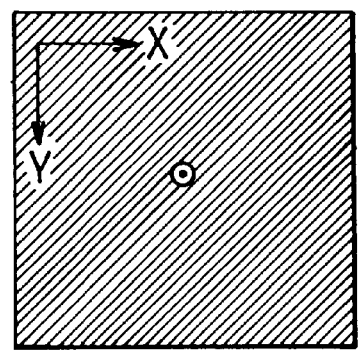
FIG. 12 is an explanatory view for three dimensional image obtained by processing the image of gradient distribution shown in FIG. 11.
Figure 13:
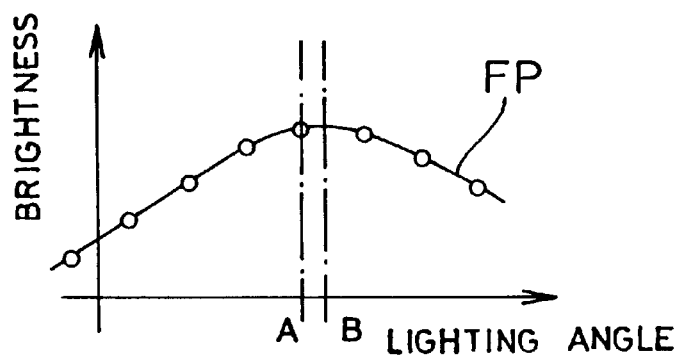
FIG. 13 is an explanatory diagram for a complementary process for precision improvement in respect of the embodiment of FIG. 1.

With the above processing, such angle distribution image RP as shown in FIG. 9 as well as such brightness distribution image RI as shown in FIG. 10 are eventually obtained. The data stored in the angle distribution image RP are the image number at which the brightness is the largest at the respective coordinates and, since the positional relationship between the TV camera, light source 2 and detection object 3 for this image number has been known with the device arrangement, the angle distribution image RP can be converted, as based on the same, into an image representing the inherent gradient of surface as shown in FIG. 11. Further, by integrating this gradient image in the direction "y" in FIG. 11, it is also possible to restore such complete three dimensional configuration as shown in FIG. 12.

While in the process of the foregoing embodiment the image number taken up as an index showing the angle of incident illumination light in producing the angle distribution image RP has been employed, a resultant resolution is limited only to the resolution of the variation in the angle of incident illumination light determined by a relative moving speed of the camera 1, light source 2 and object 3 and a taking-up intervals of the images.

As a measure for complementing this respect, there may be considered a process in which the relationship of the angle of incident illumination light and the brightness are approximated by a Gaussian function, secondary function or the like, and the peak of the brightness is obtained from the peak of such function with a resolution exceeding the moving resolution of the angle of illumination (subpixel detecting process). That is, it is possible to obtain the angle of incident illumination light providing the largest brightness at a higher resolution than in the case (A) where simply the largest value is obtained, by (B) obtaining the peak by means of the approximate function FP, and the measurement resolution is improved.

While in the aspect of FIG. 7 the positions of the TV camera 1 and of the detection object 3 are fixed and the light source 2 only is moved in the device employed, it is possible that the foregoing arrangement in which a range of each detection is limited to a size of the sight of TV camera 1 is not suitable in an event where the detection object 3 is of a large elongated surface, such as a rolled copper sheet. In that event, it is effective to employ an arrangement in which the positional relationship of the TV camera 1 and light source 2 is fixed as an integral unit and the detection object 3 or the integral unit is relatively moved to perform the measurement. A schematic arrangement of a device in an aspect employing this process is shown in FIG. 14, in which a conveyor 5 is provided for moving the detection object 3.

In an event where the object 3 is large in lateral width so as to require a large luminaire as the light source 2, the above detection means is made effective by fixing the object 3 and light source 2 and shifting the TV camera 1. A schematic arrangement of a device employing this measure is shown in FIG. 15.

Figure 14:
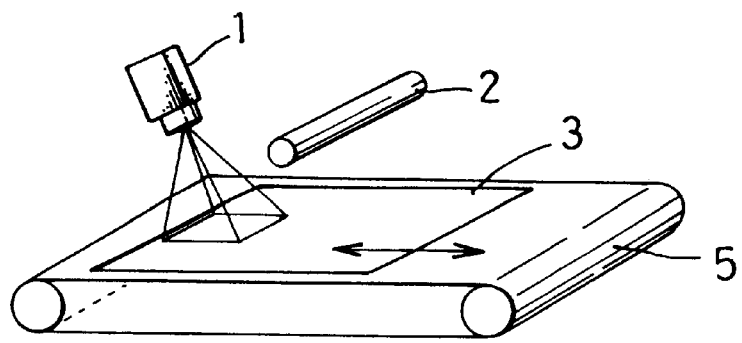
FIG. 14 is a schematic explanatory view for a device employed in performing another embodiment of the image processing process according to the present invention.

With such arrangements as shown in FIGS. 14 and 15, it is necessary to attain the correspondence of an identical point on the object 3 between respective images, since the positional relationship between the TV camera 1 and the object 3 is caused to vary unlike the arrangement in which the light source 2 is moved. While FIGS. 16(a) and 16(b) show the identical defective part B on the surface of the object 3, it will be appreciated that the part B seems to have been moved on the images due to the relative movement between the camera 1 and the object 3. Because an amount of this movement can be estimated on the basis of the velocity of the relative movement between the camera 1 and the object 3 as well as an arrangement of optical system employed, it is possible to attain the correspondence of the identical part of the object 3 between the respective images.

Figure 17:
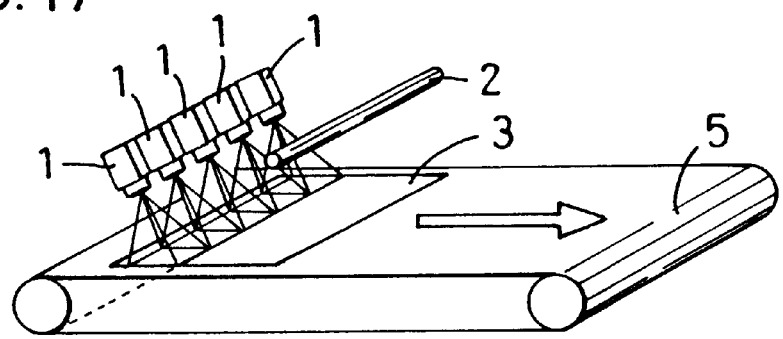
FIG. 17 is an explanatory view for a device performing another embodiment for speeding up the image processing process of the present invention.

In an event where the detection object 3 is large with respect to the TV camera 1 or a high speed processing is called for, it is possible that the single TV camera 1 will be insufficient. In such event, the problem may be removed by employing a plurality of the TV camera 1 arranged in parallel as shown in FIG. 17.

Figure 18:
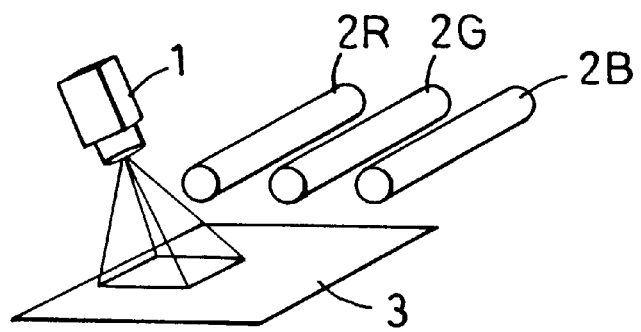
FIG. 18 is an explanatory view for a device employed in another embodiment for speeding up the image processing process of the present invention.

Further, it is possible to reduce the frequency of the image taking-up and to execute the measurement in a shorter time, by catching the direct reflection component in a plurality of colors within one sight of the TV camera 1 with a plurality of light differently colored of light emitting diode, neon tube or the like included in the light source 2, and processing these differently colored components separately through a color image processing. An arrangement of this working aspect will be as shown in FIG. 18, in which the light sources are of red color 2R, green color 2G and blue color 2B.

Figure 19:
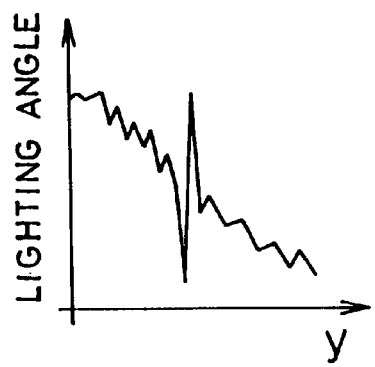
FIG. 19 is a schematic explanatory view for the image of angle distribution characteristic in the image processing process of the present invention.

In the arrangement of the foregoing embodiment of FIG. 7, such a plurality of images in which the direct reflection component gradually shifts at the flat part as shown in FIG. 8 can be obtained by moving the light source 2. The angle distribution images RP will be those which involve a gradient in vertical directions as shown in FIG. 19, since the image number in which the brightness of the respective picture elements is the largest among the images RP is regarded as the picture element value. As the detection of the defective part by means of a simple processing with threshold value or the like will be uneasy when such gradient is left as it is, a correction of the gradient will be essential. For this purpose, there may be considered two ways in arranging the device.

Figure 20:
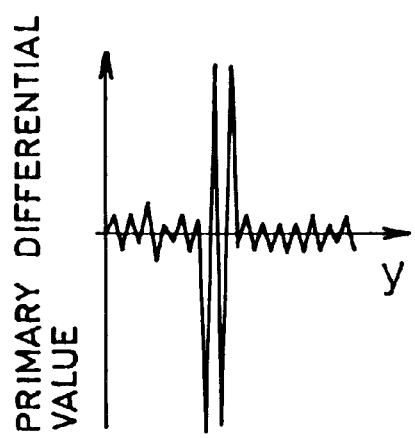
FIGS. 20 to 22 are schematic explanatory diagrams for working aspects upon performing a correction of gradient in the image processing process including a surface defect detecting arrangement in the present invention, respectively.

In a first arrangement, the occurrence of the gradient only in the vertical directions of the picture in the angle distribution images RP is utilized, and the gradient is removed through a linear differentiation in the vertical directions in the picture of the images, of which arrangement is as shown in FIG. 20. With this arrangement, the effect attainable will be that, not only the correction of the gradient, a large undulation, warp or the like in the surface of the detection object 3 can be removed, and any finely small defective part can be emphasized.

In a second arrangement, the gradient occurring in the images is preliminarily estimated with an amount of variation in the angle of incident illumination light made as the basis, and the gradient is corrected by obtaining a difference between the estimated gradient and the actual gradient in the angle distribution images RP.

Figure 21:
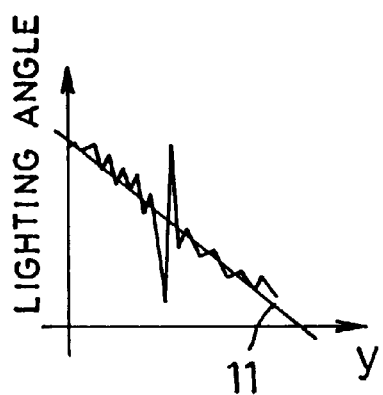
Figure 22:
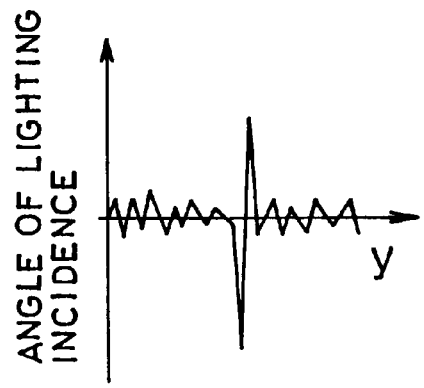

The second arrangement will be as shown in FIG. 21, according to which such gradient amount 11 as shown in FIG. 21 is substracted from the original picture element value, and the image can be rendered to be flat as shown in FIG. 22. In this arrangement, the surface undulation or warp of the object 3 cannot be removed, and the arrangement will be effective in an event when the undulation or warp is required to be detected.

Figure 23A:
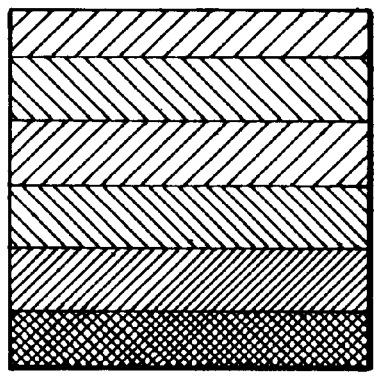
FIG. 23(a) is a schematic explanatory view for a standard image employed in a working aspect for detecting a defect in the image processing process containing the surface defect detecting arrangement in the present invention.
Figure 23B:
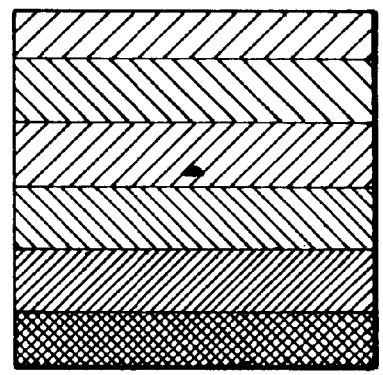
FIG. 23(b) is an explanatory view for the same inspection image as FIG. 23(a)

Next, a processing for executing the detection of actual defect with the obtained angle distribution images RP employed shall be described. As the simplest defect detection arrangement, first, measured data on non-defective article by means of the particular arrangement are preserved as a standard image, as shown in FIG. 23(a), for comparison with inspection image data, as shown in FIG. 23(b), as measured with respect to the detection object.

Figure 24A:
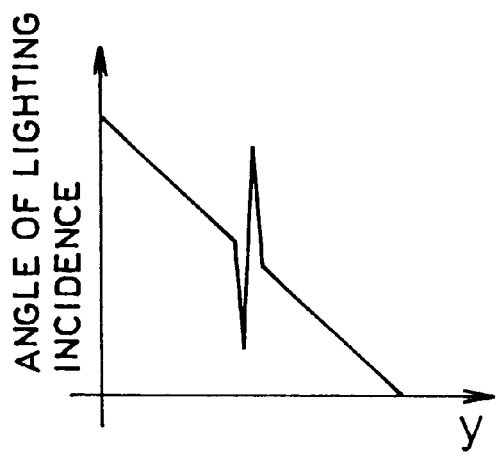
FIG. 24(a) is an explanatory diagram showing variation in illumination angle appearing in a direction perpendicular to the light source in an event when the defect is a dent.
Figure 24B:
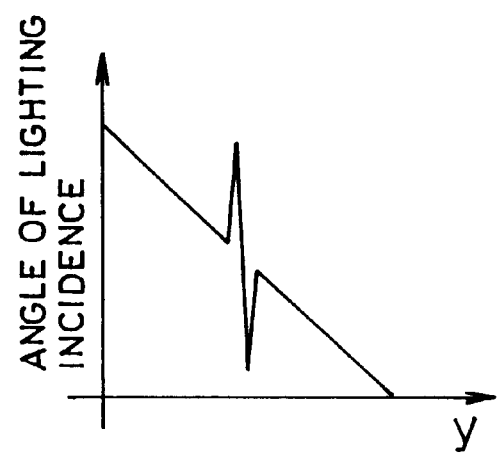
FIG. 24(b) is an explanatory diagram showing variation in illumination angle appearing in the direction perpendicular to the light source in an event when the defect is a blister.

By utilizing the data on the surface gradient and stored in the angle distribution images RP, the fine dent, blister, flaw and the like present on the surface of the detection object 3 can be detected. Further, in respect of the surface gradient data, a fluctuation in the gradient in the moving direction of the light source will be directly opposite between the dent defect and the blister defect, and the type of the defect can be discriminated with the data utilized. Variation in the angle of incident illumination light in Y-direction in FIG. 7 in the events of the dent defect and blister defect is shown in FIGS. 24(a) and 24(b).

Next, a processing for executing the detection of actual defect with the obtained brightness distribution images RI employed shall be described. In the brightness distribution images RI obtained by the arrangement as has been referred to in the above, the data on the surface reflectance of the object 3 are stored, and an analysis of these data will allow a defect accompanying the fluctuation in the brightness, that is, the flaw defect or rust defect to be detected.

Figure 25:
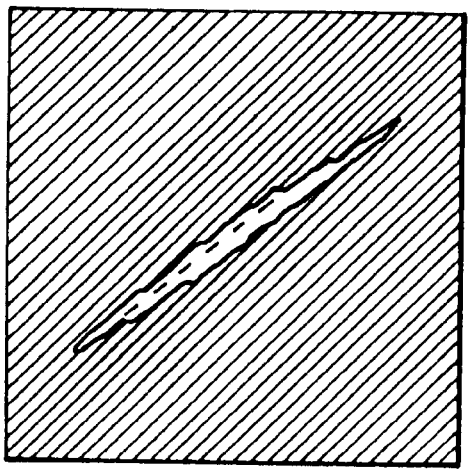
FIG. 25 is an explanatory view for a working aspect of defect detection of flaws in the image processing process including the surface defect detecting arrangement in the present invention.

The flaw defect occurs when the metal surface is scratched by any other hard object, and its surface profile shows that surface microstructure is crushed to be close to a mirror surface. Its reflectance is thus made to be very high, and appears in the form of such bright defect as shown in FIG. 25 in the obtained brightness distribution images RI. Since the flaw is characterized in occurring in linear form, and it is enabled to detect the flawish defect by extracting a part where the brightness is varying in linear form in the brightness distribution images.

Figure 26:
FIG. 26 is an explanatory view for a working aspect of defect detection of rust in the image processing process including the surface defect detecting arrangement in the present invention.

In the case of the rust defect, the surface reflectance of the metal layer is lowered due to an oxidation, so that such dark defect as shown in FIG. 26 will occur in the obtained brightness distribution image. Since the rust defect is larger remarkably in the area than other defects, any part present in the brightness distribution image with a lower brightness than surroundings and with a large area to some extent may be discriminated as the rust defect.

Figure 28:
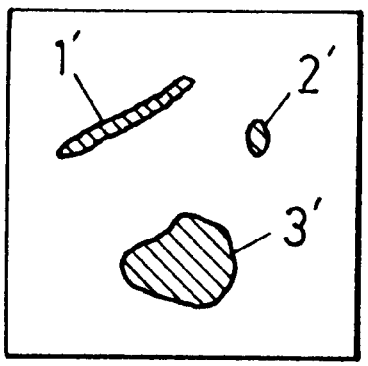
FIG. 28 is an explanatory view for a working aspect of defect detection with an area of dark spots as a reference in the image processing process including the surface defect detecting arrangement in the present invention.
Figure 29:
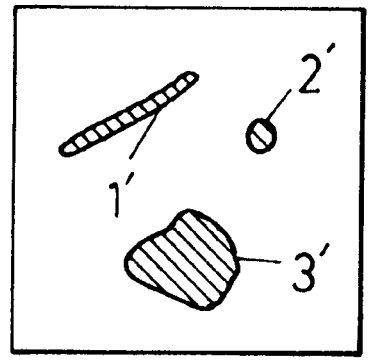
FIG. 29 is an explanatory view for a working aspect of defect detection also with an area of dark spots as a reference in the image processing process including the surface defect detecting arrangement in the present invention.
Figure 27:
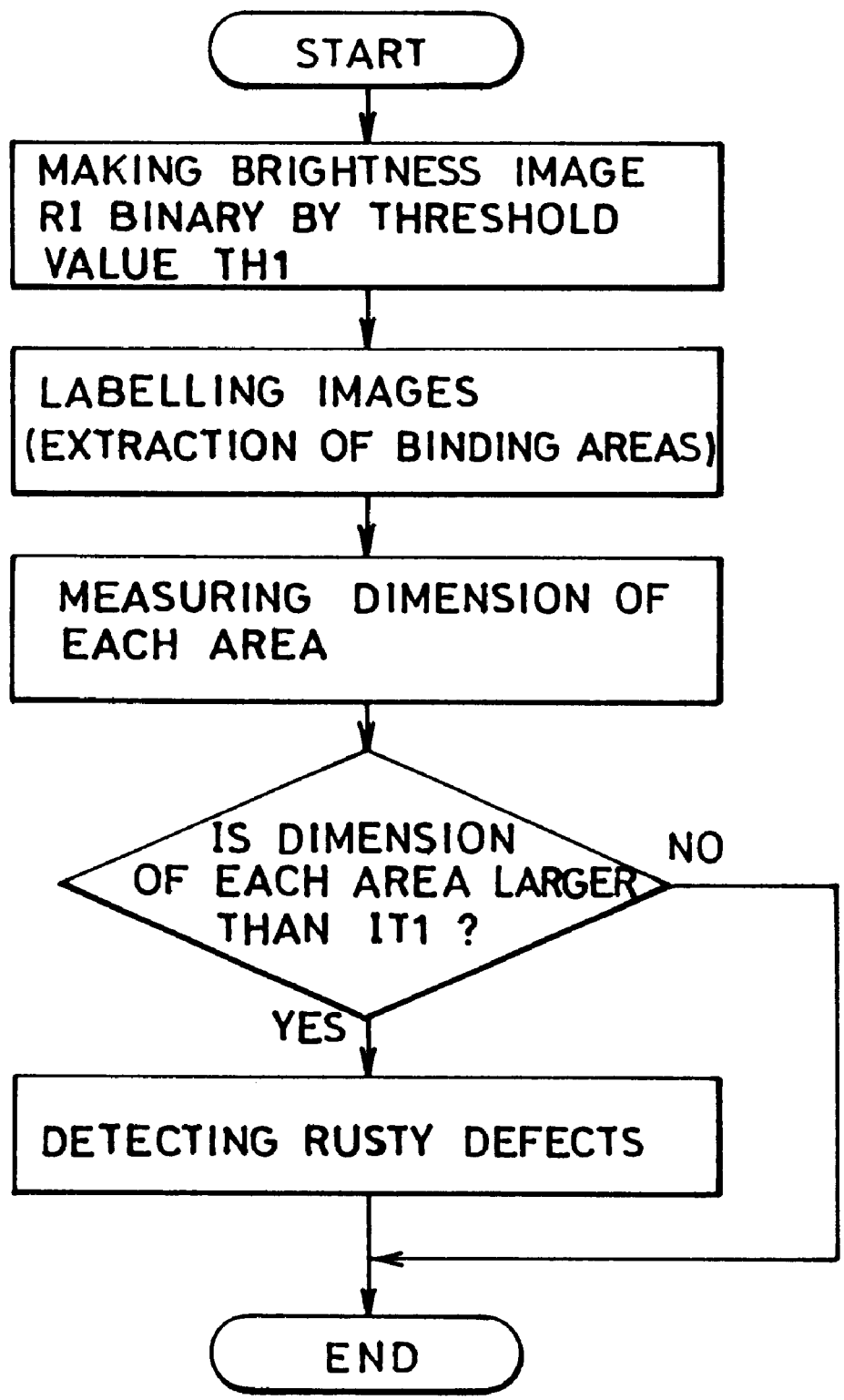
FIG. 27 is a flow chart for explaining the working aspect of defect detection of the rust in the image processing process including the surface defect detecting arrangement in the present invention.

The detecting process for the rust defect shall be described with reference to a flow chart shown in FIG. 27. First, the brightness (distribution) image RI is binary coded by a threshold value TH1. Then, certain sequential zones are extracted and numbered as shown in FIG. 28, the surface area of the respective zones extracted is obtained, and one of the zones which has an area exceeding the threshold value TH1 is regarded as the rust defect part. FIG. 29 shows a state in which the zones numbered 1 and 3 are determined to be of the rust defect.

Figure 30:
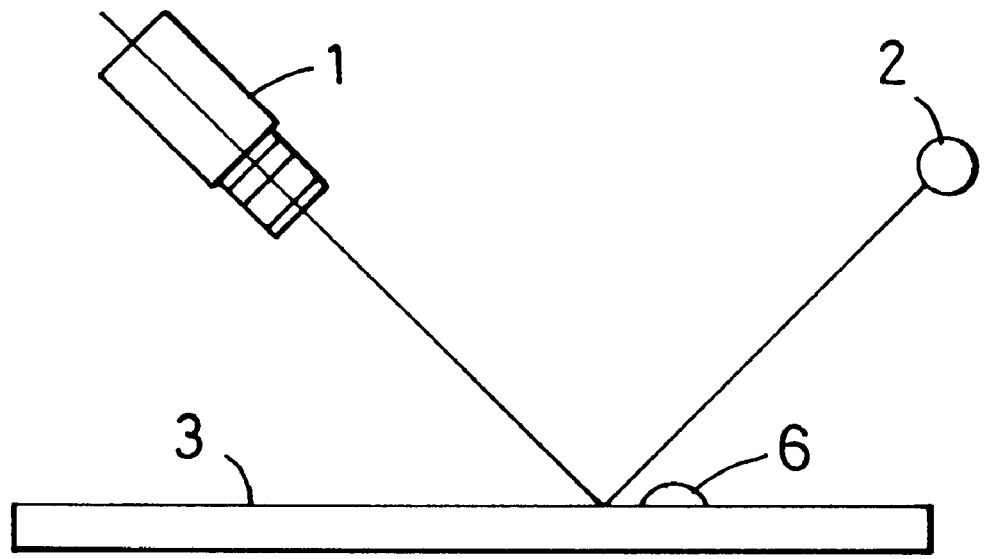
FIG. 30 is a theoretical explanatory view for a working aspect of detecting a foreign matter in the image processing process including the surface defect detecting arrangement in the present invention.
Figure 31:
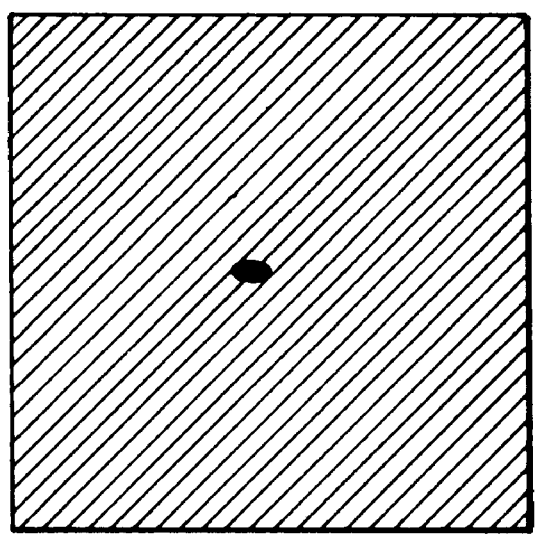
FIG. 31 is an explanatory view for the working aspect of detecting the foreign matter in the image processing process including the surface defect detecting arrangement in the present invention.

Further, in an event where a foreign matter is present on the surface of the detection object 3, the foreign matter 6 observed by the TV camera 1 appears always in silhouette because the light source 2 is present always on the opposite side with respect to the foreign matter 6 as shown in FIG. 30. Consequently, the part corresponding to the foreign matter appears in the brightness distribution image as a dark spot as shown in FIG. 31. Thus, it is enabled to discriminate the foreign matter 6 on the surface of the object from any blister defect, since the foreign matter 6 has a larger height than the blister and shows such characteristic as in the above. Since the foreign matter 6 appears as the dark spot of a small area in the brightness distribution image, a part of a lower brightness but present with a small area in contrast to the rust defect part can be discriminated as the foreign matter.

Figure 32:
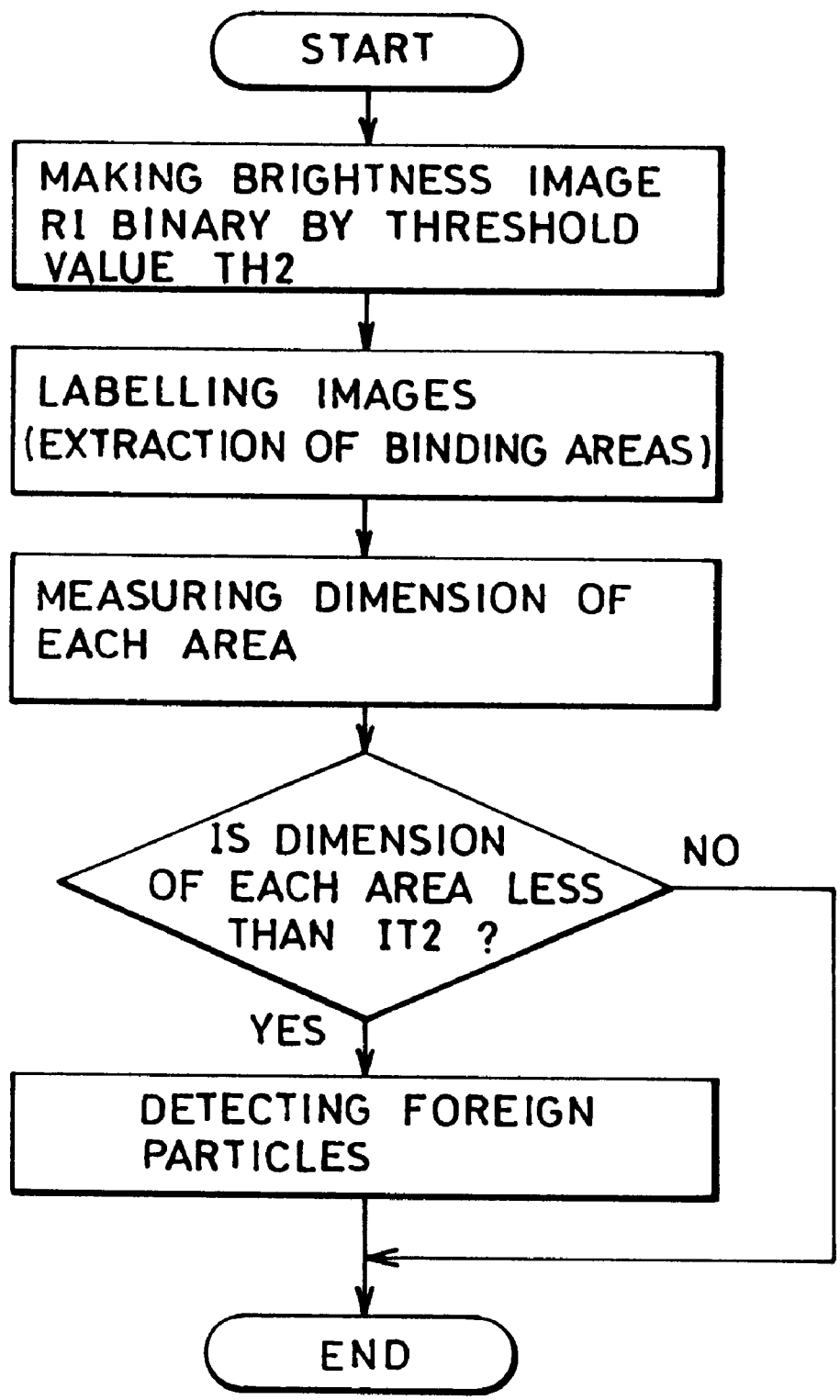
FIG. 32 is a flow chart for explaining the working aspect of detecting the foreign matter in the image processing process including the surface defect detecting arrangement in the present invention.

Referring here to the detecting process of the foreign matter 6 with reference to a flow chart shown in FIG. 32, the brightness (distribution) image RI is binary coded by a threshold value TH2 first, then sequential zones are extracted as in FIG. 28, the surface areas of these zones are obtained, and any zone or zones having the area less than the threshold value TH2 may be regarded as the foreign matter or matters. In this case, the zone numbered 2 in FIG. 29 is to be discriminated as the foreign matter 6.

What is claimed is:

1. An image processing process comprising the steps of:
disposing a TV camera for photographing an object and a light source for illuminating the object;
obtaining sequentially a plurality of images of the object with the TV camera while relatively varying positional relationship of the light source, object and TV camera so as to sequentially vary the angle of incident illumination light at a plurality of positions on the surface of the object;
obtaining a distribution of the angle of incident direct-reflection light at the time when the brightness at the same point is the largest, with respect to the plurality of images of different angles of incident illumination light; and
obtaining images showing the distribution of the angle of direct-reflection light at a plurality of predetermined points on the surface of the object of detection.

2. The process according to claim 1, wherein the light source employed is a linear light source.

3. The process according to claim 1 wherein the light source employed is a spot light source.

4. The process according to claim 1 wherein a three dimensional configuration of the object at positions corresponding to respective picture elements of the images is obtained, with the angle of incident direct-reflection light at the same position on the object made as a reference.

5. The process according to claim 1 wherein the correspondence is attained for the same position on the object on the basis of relative positional relationship of the object to the TV camera, between the plurality of images photographed by the TV camera.

6. The process according to claim 1 wherein an interpolation processing is performed on the basis of a brightness data on the images before and after the image showing the largest brightness, in storing the angle of incident direct-reflection light at the same position on the object.

7. The process according to claim 1 wherein the images of the distribution of angles are subjected to a linear differentiation in a direction in which observed direct-reflection component moves.

8. The process according to claim 1 wherein, in the angle distribution images, a gradient of picture element value occurring in moving direction of the direct-reflection component observed is corrected on the basis of a range in which the angle of incident illumination light varies.

9. The process according to claim 1 wherein the positional relationship between the TV camera and the object is fixed, and the light source is moved to sequentially vary the angle of incident illumination light at the respective positions on the object.

10. The process according to claim 1 wherein the positional relationship between the TV camera and the light source is fixed, and the object is moved to sequentially vary the angle of incident illumination light at the respective positions on the object.

11. The process according to claim 1 wherein the positional relationship between the object and the light source is fixed, and the TV camera is moved to sequentially vary the angle of incident illumination light at the respective positions on the object.

12. The process according to claim 1 wherein a plurality of the TV cameras are used simultaneously.

13. The process according to claim 1 wherein a plurality of the light sources of mutually different colors are employed.

14. The process according to claim 1 wherein, when the object is a rolled metal, the TV camera is disposed to have a direction of observation aligned with a direction of streaks made on the rolled metal.

15. An image processing process comprising the steps of:
preparing a TV camera for photographing an object and a light source for illuminating the object;
obtaining a plurality of images of the object by the TV camera while relatively varying the positional relationship between the light source, object and TV camera to sequentially vary the angle of incident illumination light at respective positions on the surface of the object;
obtaining a distribution of angles of incident direct-reflection light at the time when the brightness at the same point is the largest, with respect to the plurality of images of different angles of incident illumination light;
obtaining angle distribution images showing a distribution of the angles of incident direct-reflection light at many predetermined points on the surface of the object; and
determining a defective part on the surface of the object by discriminating through the angle distribution images.

16. An image processing process comprising the steps of:
preparing a TV camera for photographing an object and a light source for illuminating the object;
obtaining a plurality of images of the object by the TV camera while relatively varying the positional relationship between the light source, object and TV camera to sequentially vary the angle of incident illumination light at respective positions on the surface of the object;
obtaining a distribution of angles of incident direct-reflection light at the time when the brightness at the same point is the largest with respect to the plurality of images of different angles of incident illumination light;
obtaining brightness distribution images showing a distribution of the brightness at the angle of incident direct-reflection light at desired many points on the surface of the object; and
determining a defective part on the surface of the object by discriminating through the brightness distribution images.

17. The process according to claim 15 wherein, in the angle distribution images, the type of the defective part is discriminated on the basis of variation in the angle of incident direct-reflection light at positions adjacent to the defective part.

18. The process according to claim 16 wherein, in the brightness distribution images, the type of the defective part is discriminated by detecting part where a variation in the brightness occurs in linear shape.

19. The process according to claim 16 wherein the type of the defective part is discriminated by providing a reference value of the area of the defective part, and detecting a part in which picture elements remarkably different in the brightness from a standard brightness are sequentially present with a larger area than the reference value.

20. The process according to claim 16 wherein the type of the defective part is discriminated by providing a reference value of the area of the defective part, and detecting a part in which picture elements remarkably different in the brightness from a standard brightness are sequentially present with a smaller area than the reference value.

* * * * *